United States Patent [19]

Langer et al.

[11] 4,396,762

[45] Aug. 2, 1983

[54] HEPARINASE DERIVED ANTICOAGULANTS

[75] Inventors: Robert S. Langer; Robert J. Linhardt, both of Somerville; Charles L. Cooney, Brookline, all of Mass.; Gerald Fitzgerald, York, Pa.; Arthur Grant, Newton, Mass.

[73] Assignee: Massachusetts Institute of Technology, Cambridge, Mass.

[21] Appl. No.: 295,914

[22] Filed: Aug. 24, 1981

[51] Int. Cl.³ .............................................. C08B 37/10
[52] U.S. Cl. ..................................... 536/21; 424/183; 424/269; 424/850
[58] Field of Search ....................... 435/268, 269, 850; 424/183; 536/21, 54

[56] References Cited

U.S. PATENT DOCUMENTS

| 3,766,167 | 10/1973 | Lasker et al. | 435/232 X |
| 4,281,108 | 7/1981 | Fussi | 424/183 X |
| 4,303,651 | 12/1981 | Lindahl et al. | 424/183 |

*Primary Examiner*—Robert A. Yoncoskie
*Attorney, Agent, or Firm*—Arthur A. Smith, Jr.; Paul J. Cook

[57] ABSTRACT

There is disclosed a heparin product obtained by degradation of heparin with heparinase from *Flavobacterium heparinum* (ATCC 13125) or mutants thereof having activity to reduce the coagulation activity of factor X while not effecting the coagulation activity of thrombin.

5 Claims, No Drawings

HEPARINASE DERIVED ANTICOAGULANTS

The Government has rights in this invention pursuant to Grant Number NIH-5-R01-GM25810-02 awarded by the U.S. Department of Health and Human Services.

BACKGROUND OF THE INVENTION

This invention relates to novel anticoagulant compositions prepared by treating heparin with heparinase.

Heparin is used during many medical and surgical procedures to anticoagulate patients. Heparin acts to block the coagulation cascade at various sites by interfering with a multiplicity of specific blood factors including factor X and thrombin.

It would be desirable to provide an anticoagulant which acts specifically on some but not all of the blood factors in the coagulation cascade. Such an anticoagulant would be useful clinically to treat patients having an excess of one or some of the blood coagulation factors while being inactive toward the other coagulation factors which are not produced in excess. Furthermore, such an anticoagulant would be useful clinically to assay for a specific blood coagulation factor. In addition, it would be desirable to provide such an anticoagulant having a smaller molecular weight and size than heparin since they would be capable of having a different bioavailability, clearance rates or pharmacokinetic profile than heparin.

It has been proposed in U.S. Pat. No. 3,766,167 by Lasker to utilize an anticoagulant derived by treating heparin with a mixture of heparinase enzymes. The anticoagulant material has a molecular weight of about 5300 daltons.

SUMMARY OF THE INVENTION

This invention is based upon the discovery that polysaccharides produced by digesting heparin with purified heparinase are capable of reducing the activity of factor X coagulation factor while not affecting the coagulation activity of thrombin. The heparinase utilizing the present invention is prepared by fermentation of *Flavobacterium heparinium* (ATCC 13125) or mutants thereof which are described in copending patent application, Ser. No. 180,780, filed Aug. 25, 1980 for "Process for Producing Heparinase" which is incorporated herein by reference. The digested heparin is fractionated to recover a polysaccharide mixture having an average molecular weight of between about 700 and about 1320. The polysaccharide mixture can be further separated to isolate a tetrasaccharide fraction, a hexasaccharide fraction and an oligosaccharide fraction. The mixture and the separated fractions all have activity to reduce the coagulating activity of factor X.

DESCRIPTION OF SPECIFIC EMBODIMENTS

The compositions of this invention are characterized by having anticoagulant activity against factor X of the coagulation cascade, while having no anticoagulant activity against the thrombin in the coagulation cascade. The compositions of this invention are obtained by degrading heparin with heparinase obtained from *Flavobacterium heparinium* (ATCC 13125) or mutants thereof as disclosed in the above-identified Ser. No. 180,780, filed Aug. 25, 1980. The degradation products of heparin having the desired activity comprised either in a mixture of degradation products having an average molecular weight between about 700 and about 1300, and an average saccharide chain size of between about 2.5 and about 3.5 Other compositions of this invention comprise saccharide products isolated from the above saccharide mixture. These saccharide products can comprise a tetrasaccharide having a molecular weight between about 1000 and about 1500 and an average chain size of 4, a hexasaccharide having a molecular weight between about 1700 and about 2200 and a chain size 6 or an oligosaccharide having a chain size equal to or greater than 8 and a molecular weight between about 2200 and about 4000.

The heparin degradation products are prepared utilizing heparinase (Heparin Lyase E. C. 4.2.2.8.) fermentatively prepared from a Flavobacterium heparinium such as *Flavobacterium heparinium* (ATCC 13125) or mutants thereof. The heparinase is purified utilizing an exchange chromatography as disclosed in U.S. Ser. No. 180,780, filed Aug. 25, 1980 and then is immobilized in accordance with the procedure set forth in U.S. Ser. No. 196,720, filed Oct. 14, 1980, for "Process and Composition for Neutralizing Heparin", which is incorporated herein by reference. The degradation products are prepared by the action of the Sepharose-immobilized purified heparinase or non-immobilized purified heparinase or heparin. The preparation usually is performed using the enzyme with a protein concentration of between about 0.05 and 5.0 g/L having a specific activity of 50 to 500 mg heparin degraded/mg protein-h and a heparin (either as the free heparin or a salted heparin) concentration of between about 1.0 and 100 g/L in a buffer solution at a pH of between 5 and 8. The buffer solution is usually comprised of a salt of phosphate, acetate or borate, such as sodium acetate, sodium phosphate, or sodium borate or the corresponding potassium or ammonium salts or the like at a concentration of from about 0.01 M to about 0.05 M. The heparin digested can be a porcine, bovine or whale heparin or the like. The digestion generally is carried out to completion but can be stopped at intermediate stages of reaction and the products can then be isolated. The complete digestion usually takes between about 0.1 and 100 hours and is dependent upon the concentration of both the heparin and the activity and concentration of the heparinase. The length of digestion time also is dependent upon temperature, with a temperature between about 10° and about 40° C. being useful, preferable about 30° C.

After the degradation products have been formed, the immobilized enzyme is removed from the mixture by filtration and the resultant product, if desired, can be reduced in volume by product precipitation or by drying, with freeze drying being the preferred method of concentration. The products thus obtained then are added to an aqueous solution such as distilled water, 0.03 M hydrochloric acid, or a salt solution which then is added to a gel column at a high concentration, usually between about 50 and about 500 g/L. The columns are packed with any conventional chromotography gel beads of controlled pore size, usually Sephadex G10, G15, G25, G50 or G75 and then can be eluted with either a buffer, distilled water or an aqueous solution of hydrochloric acid at a concentration between about 0.01 M to about 0.1 M. The columns effect fractionation of the heparin digestion products by size and appropriate molecular weight markers, such as carbohydrates, including glucose, maltose, and raffinose, or polyethylene glycols of defined molecular weight are used as molecular weight standards.

Further fractionation can be accomplished by loading from about 0.001 to about 1.0 mg of heparin digestion products onto a high pressure liquid chromotography column packed with uncoated silica and eluted with a salt solution such as sodium chloride of from about 0.001 M to about 0.1 M. The column acts to separate the products on the basis of charge.

The anticoagulant activity of the fractionated heparin digestion products thus obtained, as well as the original mixture of heparin digestion products can be measured using standard clinical assays, such as activated prothrombin time (APTTX), Factor X clotting time (FX), whole blood recalcification time (WBRT) and the chromogenic assay or Thrombin-Antithrombin III binding (TAT). The composition of completely degraded heparinase digestion products (as sodium salts) and their properties as shown in Table I.

TABLE I

| Sample | Chain Size | Molecular Weight | Amount Mol %, Wt % | % of Heparin's metachromatic activity by Azure A | Wt % of Heparin's Anticoagulant Activity By: | | | |
|---|---|---|---|---|---|---|---|---|
| | | | | | FX | TAT | APTT | WBRT |
| Heparin (Porcine mucosal sodium salt) | Avg. of 34 | Avg. 11,500 | 100, 100 | 100 | 100 | 100 | 100 | 100 |
| Heparin Digestion Products Unfractionated | Avg. of 2.7 | Avg. 903 | 100, 100 | 20 | 25 ± 5 | 0 | 0 | 0 |
| disaccharide | 2 | 669 | 53.6, 31.4 | 0 | 0 | 0 | 0 | 0 |
| tetra-saccharide | 4 | 1323 | 27.6, 32.3 | 1.0 | 1.3-3.1 | 0 | 0 | 0 |
| hexa-saccharide | 6 | 1977 | 15.2, 26.8 | 13.8 | 3.75 ± .06 | 0 | 0 | 0 |
| oligo-saccharide | ≧8 | Avg. 2950 | 3.6, 9.6 | 5.2 | 2.4 ± .06 | 0 | 0 | 0 |

Useful products in accordance with this invention also can be prepared by partial digestion of heparin and either used as a mixture or fractionated in the same manner as are the completely digested products. The properties of the unfractionated mixture of products obtained at various stages in the digestion are shown in Table II.

TABLE II

| % Time completion of Heparin Digestion | Wt % of Heparin's Anticoagulant Activity | | | % of Heparin's metachromatic activity by Azure A |
|---|---|---|---|---|
| | FX | TAT | WBRT | |
| 0 | 100 | 100 | 100 | 100 |
| 4 | 85 | 100 | 85 | 86 |
| 12.5 | 60 | 40 | 45 | 60 |
| 30 | 40 | 12 | 10 | 45 |
| 100 | 25 | 0 | 0 | 20 |

As noted above, the compounds of this invention can be isolated in the form of the sodium salt. However, it is to be understood that the compounds of this invention can be utilized in the form of free acids or other metallic salts or other acid addition salts. Representative suitable salts include the alkaline metal and alkaline earth metal bases, preferable hydroxide, while the acid addition salts which may be utilized include hydrochloric, sulfuric, phosphoric, citric acids or the like. These salts can be formed by any conventional means.

The composition of this invention can be utilized for assays to determine concentration of factor X or can be utilized therapeutically by being administered to a patient in any suitable form, such as orally, intravenously, intraperitoneally, intermuscurlly, or sublingually intranassally The following examples illustrate the present invention and are not intended to limit the same.

EXAMPLE I

Heparin digestion products were prepared in a mixture of porcine mucusal heparin (50 g/L), heparinase immobilized on Sepharose 4B (66 g bed/L, 10 g protein/g bed using enzyme with a specific activity of 100 mg of heparin degraded/mg protein-h) all in buffer consisting of 0.25 M sodium acetate and 0.0025 M calcium acetate. The mixture then was shaken at 30° C. for 10 hours until the digestion was completed and samples were taken intermittently to monitor the reaction and to measure the anticoagulant activity of partially digested heparin.

EXAMPLE II

The digestion products obtained, as described in Example I, were concentrated by freeze-drying. A concentrated sample (1.5 ml of 333 g/L) of heparin digestant products were loaded onto a Sephadex G15 column (300 cm×100 cm) and eluted at a flow rate of 0.13 ml/min, using either 0.03 M hydrochloric acid or distilled water and monitored at 232 nm. Two fractions were isolated, i.e., disaccharide fraction and a higher molecular weight fraction. These fractions were again concentrated by freeze-drying. The disaccharide was run a second time on the same column and under the same conditions giving a single peak. The higher molecular weight heparin digestion products were loaded in a 1.5 ml volume onto a second column (2 cm×40 cm), packed with Sephadex G50 and eluted with 0.03 hydrochloric acid, resulting in 3 fractions representing tetrassacharide, hexasaccharide and oligosaccharide products.

Each of the products fractionated in the above fashion gave only one peak when injected onto a High Pressure Liquid Chromatography Column (HPLC) fitted with an unsilated silica column and eluted with aqueous sodium chloride (0.15 M) at pH 5.8 at 1 ml/min. Retention times of 5.1, 4.8, 4.6, 4.3 minutes were obtained for the di, tetra, hexa and oligo saccharide products respectively.

EXAMPLE III

These heparin degradation products obtained, as described in Examples I and II, were prepared for assay by removing buffer salts using the Sephadex G15 column described in Example I and eluting with distilled water. Each product, as well as the unfractionated product mixture, was freeze-dried and weighed. A sample comprising each product (di, tetra, hexa and oligo saccharide), the unfractionated mixture (containing all the product fractions) and the heparin from which the products were derived were assayed by standard procedures for anticoagulant activities and metachromasia activity, as shown in Table I.

We claim:

1. An anticoagulant composition effective to reduce the coagulant activity of factor X, while being ineffective to reduce the coagulant activity of thrombin said composition being produced by digesting heparin with a purified heparinase obtained from *Flavobacterium heparinum* (ATCC 13125) or mutants thereof and comprising degradation products from said digestion selected from the group consisting of a mixture of saccharides, having an average chain size of between about 2.5 and about 3.5, an average molecular weight of between about 700 and about 1320, a tetrasaccharide isolated from said mixture having a chain size of 4 and a molecular weight between about 100 and about 1500, a hexasaccharide isolated from said mixture having a chain size of 6 and a molecular weight between about 1700 and 2200 and an oligosaccharide composition isolated from said mixture having a chain size equal to or greater than 8 and having an average molecular weight between about 2200 and about 4000.

2. The composition of claim 1 comprising said mixture of saccharides.

3. The composition of claim 1 comprising said tetrasaccharide.

4. The composition of claim 1 comprising said hexasaccharide.

5. The composition of claim 1 comprising said oligosaccharide.

* * * * *